United States Patent
Ruffa

(10) Patent No.: US 8,188,638 B2
(45) Date of Patent: May 29, 2012

(54) COOLING ACOUSTIC TRANSDUCER WITH HEAT PIPES

(75) Inventor: Anthony A. Ruffa, Hope Valley, RI (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 429 days.

(21) Appl. No.: 12/462,061

(22) Filed: Jul. 27, 2009

(65) Prior Publication Data

US 2011/0018395 A1     Jan. 27, 2011

(51) Int. Cl.
*H01L 41/08* (2006.01)
(52) U.S. Cl. .......... 310/334; 310/337; 310/341
(58) Field of Classification Search .......... 310/334, 310/337, 338–339, 311, 343, 312, 325, 346, 310/328, 323.12, 342; 367/174, 158; *H01L 41/08*
See application file for complete search history.

(56) References Cited

U.S. PATENT DOCUMENTS

| 4,031,418 | A | * | 6/1977 | Cluzel et al. | 367/158 |
| 5,155,709 | A | * | 10/1992 | Flanagan et al. | 310/337 |
| 5,515,343 | A | * | 5/1996 | Boucher et al. | 310/337 |

\* cited by examiner

*Primary Examiner* — Walter Benson
*Assistant Examiner* — Karen B Addison
(74) *Attorney, Agent, or Firm* — James M. Kasischke; Michael P. Stanley; Jean-Paul A. Nasser

(57) ABSTRACT

A transducer with a closed heat pipe is provided with a hot surface and a cold surface. The hot surface is in contact with the transducer interior and the cold surface is in contact with a cooler contact area. A fluid is used in the pipe which boils at the temperature of the hot surface and condenses at the temperature of the cold surface. A wick inside the heat pipe facilities the return by capillary action of the condensed fluid to the hot end. The heat pipe can be evacuated to adjust the boiling temperature of the fluid. A variant involves drilling additional holes into ceramic rings and inserting heat pipes. Increasing the heat pipe length into the tail mass and the piston increases the cool region for the fluid to condense; thereby improving the performance of the transducer.

11 Claims, 3 Drawing Sheets

COOLING ACOUSTIC TRANSDUCER WITH HEAT PIPES

STATEMENT OF GOVERNMENT INTEREST

The invention described herein may be manufactured and used by or for the Government of the United States of America for governmental purposes without the payment of any royalties thereon or therefor.

CROSS REFERENCE TO OTHER PATENT APPLICATIONS

None.

BACKGROUND OF THE INVENTION (1) Field of the Invention

The present invention utilizes heat pipe technology to cool the ceramic used in transducers and acoustic projectors.

(2) Description of the Prior Art

It is known in the art that transducers, designed to project acoustic power, are often limited by the build-up of internal heat generated in an active piezoelectric ceramic as a result of dielectric losses. High internal temperatures can adversely change material properties, increasing losses, possibly causing de-poling, and reducing reliability and performance. A variety of cooling methods are used to address the heat dissipation problem.

In Cluzel et al. (U.S. Pat. No. 4,031,418), a piezo-electric transducer for low frequency acoustical waves comprising a stack of piezo-electric elements and alternating electrodes disposed between a front receiver plate and a counter mass. The counter mass comprises a rigid annular block surrounding the stack, a rear plate engaging the rear of the stack and an elastic connection between the block and the rear plate.

In Snyder (U.S. Pat. No. 5,721,463), a device is disclosed for improving thermal transfer inside an ultrasound probe and reducing heat build-up near the transducer face. The cable components are used as heat conductors which conduct heat out of the probe handle. They are coupled in an internal heat conductor which is in a heat conductive relationship with the transducer pallet. Thus, heat generated by the transducer array can be transferred, via the heat conductor plate and the cable heat conductors, away from the probe surface. A heat conductive structure can be embedded in the overall shield braid of the cable. Suitable heat conductive structures include thread or wire made of material having a high coefficient of thermal conductivity, as well as narrow tubing filled with heat conductive fluid. Alternatively, inlet and return flow paths for cooling fluid are incorporated in the cable. The inlet and return flow paths inside the cable are respectively connected to the inlet and outlet of a flow path which is in heat conductive relationship with an internal heat conductor in the probe handle.

In Austin et al. (U.S. Pat. No. 5,884,693), a passive cooling system is disclosed for cooling an enclosure containing electronic components. A hollowed portion of the enclosure is formed as an integral heat pipe containing a working fluid. The hollowed portion has an evaporator section located at the top and a condenser section located at the bottom. The enclosure also has hollowed side walls which serve as passageways for the working fluid to flow through in between the evaporator and condenser sections. Gravity and the pressure of evaporation force the working fluid down to the condenser section. A wick is provided for returning the working fluid to the evaporator section by capillary action. Additionally, an ultrasonic transducer driven by the heat rejected from the condenser section may be used to help return the working fluid to the evaporator section. Finally, a check valve may be employed before the evaporator section for the working fluid to fluid.

In Kelly, Jr. et al (U.S. Pat. No. 5,961,465), an ultrasound transducer structure is disclosed which includes: an ultrasound transducer operable to generate and receive ultrasonic energy, a communication cable, integrated circuits for processing signals received from said ultrasound transducer and flexible circuits for connecting the communication cable to the integrated circuits to the ultrasound transducer. A housing contains the ultrasound transducer, the integrated circuits and the flexible circuits. A heat transfer structure is positioned within the housing and is in contact with the integrated circuit. A heat conductor resides in contact with the heat transfer structure and conducts heat generated by the integrated circuits to a heat sink.

In Kan et al (U.S. Pat. No. 6,528,909), a spindle motor assembly is disclosed which has a shaft with an integral heat pipe. The shaft with the integral heat pipe improves the thermal conductively of the shaft and the spindle motor assembly. The shaft includes an elongated portion and a sealing structure. For one embodiment, the sealing structure includes a cap and a gasket that are joined to the shaft by a brazing process.

Baumgartner et al (U.S. Pat. No. 7,017,245), a method is disclosed for manufacturing a multi-layer acoustic transducer with reduced total electrical impedance. The method is based on the bonding of two piezoelectric ceramic layers with confronting metalized surfaces to a thin electrical conductor, then electrically connecting the top and bottom surfaces to form a wrap-around electrode while a center conductor forms a second electrode. The total electrical impedance of a two-layer ceramic stack comprised of piezo-electric layers connected in this manner is one-fourth that of a solid ceramic layer of the same size. This provides for better matching of the acoustic stack impedance to that of the electrical cable, increased penetration depth for imaging within the body, and improved acoustic element sensitivity.

In regard to the references above, heat pipes having a wick are taught for a metal shaft in an electric motor (U.S. Pat. No. 6,528,909), which could be construed as substantially equivalent to a hollow bolt in the Tonpilz design (a hollow bolt may have synergistic benefits and this would not be the case for a shaft). U.S. Pat. No. 5,884,693 discloses a passive cooling system for cooling an enclosure containing electronic components; however, no combination of the cited references suggests or teaches all of the elements of the acoustic transducer cooled with heat pipes in such a manner that would be predictable to one skilled in the art.

Such a heat pipe would be a closed tube with a working fluid that vaporizes at the hot end and condenses at the cold end; thereby, transferring large amounts of heat by removing the latent heat of vaporization at the hot end and adding the heat at the cold end. Furthermore, no transducer in any of the transducers of the prior art contains off-center heat pipes.

Most transducer packages involve a stack of active ceramic. A Tonpilz transducer 10 in the prior art, as depicted in FIG. 1, consists of a stack of ring elements 12. Pre-stressed by a center bolt 14 with a radiating piston 16 on one end (the radiating piston is in contact with the surrounding water and radiates acoustic energy into the water by vibrating at acoustic frequencies). The other end of the radiating piston 16 is connected to a tail mass 18. The tail mass 18 governs the resonant frequency, which is $(k/m)^{1/2}$ (where k and m are the effective stiffness and mass, respectively, of the transducer)

and is heavy compared to the radiating piston 16 so that the tail mass reduces recoil as a result of the motion of the radiating piston.

Typical attempts at thermal management involve heat-sinking the stack ends to the highly thermally-conductive piston 16 and end mass (e.g., constructed from aluminum). The piston 16 is in contact with (relatively cool) surrounding fluid.

The center bolt 14 pre-stresses the ceramic in order to prevent the ceramic from going into tension during operation; otherwise, the tension would cause the ceramic to break. The stiffness of the center bolt 14 must be small compared to the stack stiffness to avoid restraining the motion of the end masses and increasing the resonant frequency.

Another common design for transducer cooling is a flex-tensional transducer 20, shown in the prior art of FIG. 2. In the figure, a ceramic stack 22 drives a shell 24; thereby, leading to larger displacement of the surrounding fluid because of the shell geometry. The ceramic stack 22 expands and contracts because of the piezo-electric effect. This expansion of the ceramic stack 22 causes the shell to expand and contract against the surrounding fluid with the result of radiating acoustic energy. The shell 24 also keeps the ceramic stack 22 in compression.

SUMMARY OF THE INVENTION

It is therefore a general purpose and primary object of the present invention to provide heat pipe technology to cool the ceramic used in acoustic projectors.

To attain the object of the present invention, a heat pipe is provided as a closed tube with a lower end and an upper end that are respectively in contact with a hot surface and a cold surface. The hot surface is in contact with the interior of the transducer, and the cold surface is in contact with the surrounding water, or a cooler part of the transducer. A working fluid is used in which the fluid will boil at the temperature of the hot surface and condense at the temperature of the cold surface.

A wick on the inside of the heat pipe facilities the return of the condensed fluid to the hot end. The wick is primarily needed when the fluid must return by capillary action against gravity. The heat pipe can be evacuated to adjust the boiling temperature of the working fluid and, by extension, the effective temperature range.

A variant of the present invention involves drilling additional holes into ceramic rings of the piezoceramic stack and inserting heat pipes. The heat pipes can be comparatively small in diameter compared to the diameter of the stack. Furthermore, increasing the length of the heat pipe into the tail mass and the piston also increases the length of the "cool" region for the working fluid to condense; thereby improving the performance of the heat pipe.

A further variant of the present invention (involving flex tensional transducers) involves a heat pipe either in the center or in multiple locations in the ceramic rings to conduct heat to the shell. This use of heat pipes in the flex tensional transducer has the advantage that both ends of the heat pipe are thermally "shorted" to the surrounding fluid, but the disadvantage of a shorter "cool" region for the heat pipe.

BRIEF DESCRIPTION OF THE DRAWINGS

A more complete understanding of the invention and many of the attendant advantages thereto will be readily appreciated as the same becomes better understood by reference to the following detailed description when considered in conjunction with the accompanying drawings wherein like reference numerals and symbols designate identical or corresponding parts throughout the several views and wherein.

DETAILED DESCRIPTION OF THE INVENTION

The slender ceramic stack geometry and thermal profile of a typical transducer make the transducer ideally suited to cooling by means of heat pipes. Heat pipes use changes of phase to achieve a very high rate of heat transfer.

Figure 1:
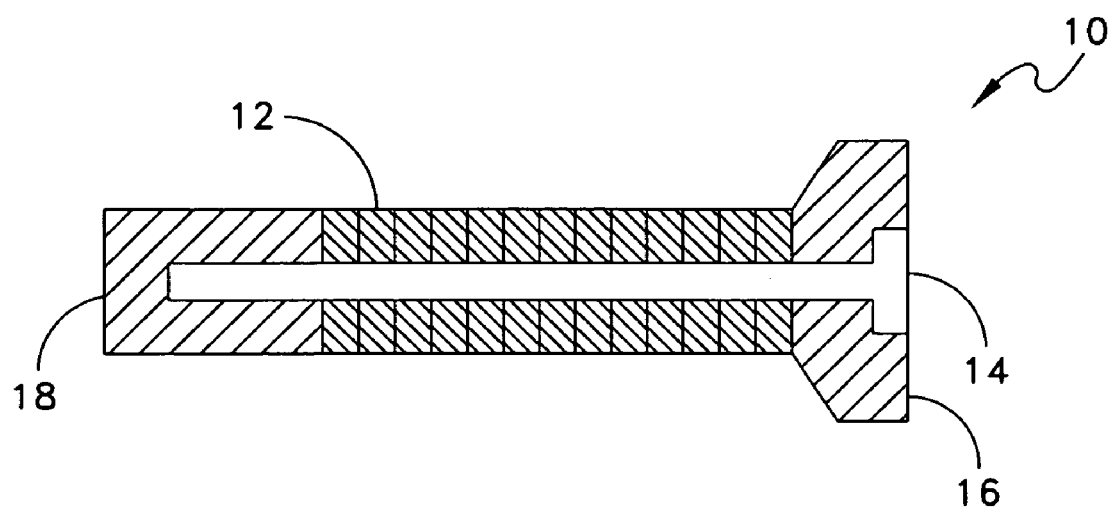
FIG. 1 is a prior art depiction of a Tonpilz transducer design.
Figure 2:
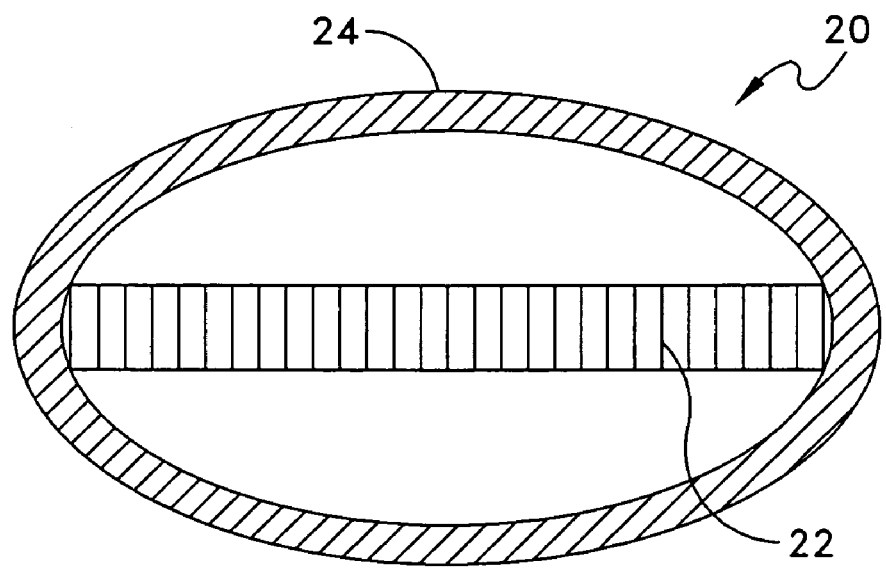
FIG. 2 depicts a prior art flex-tensional transducer design.
Figure 3:
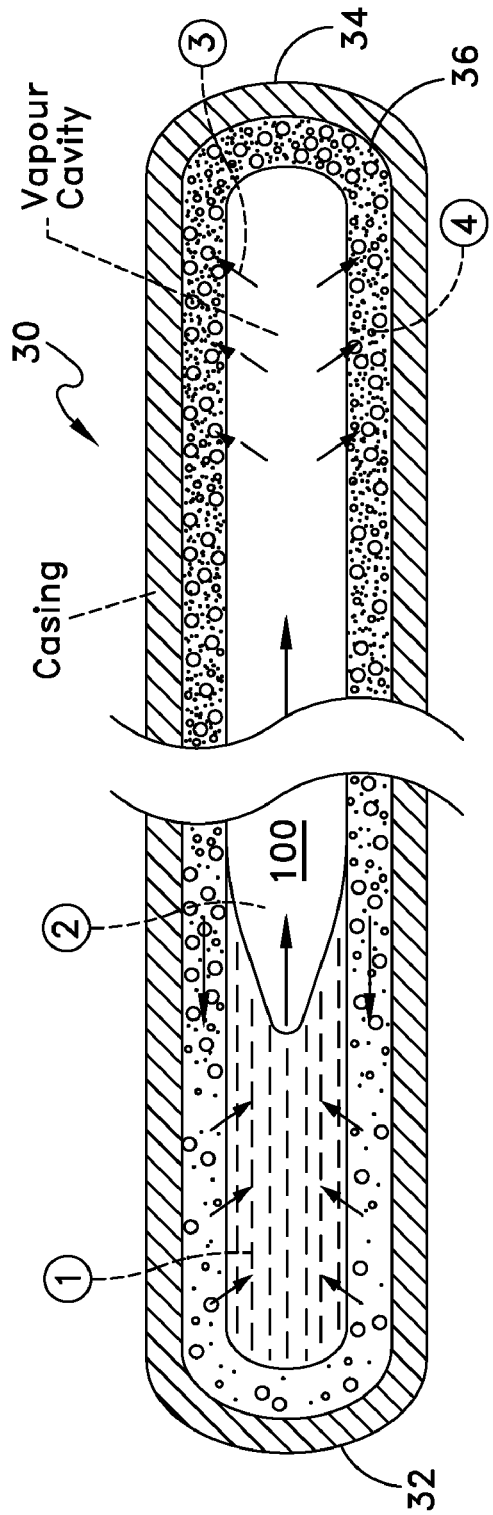
FIG. 3 depicts a heat pipe of the present invention.

A heat pipe 30 of the present invention is shown in FIG. 3. In the figure, the heat pipe 30 includes a closed tube whose lower end 32 and an upper end 34 are respectively in contact with a hot surface and a cold surface. The hot surface is in contact with the interior of the transducer, and the cold surface is in contact with the surrounding water, or a cooler part of the transducer (closer to the surrounding water). A working fluid 100 (such as ammonia, alcohol, ethanol, water or some combination thereof) is used in which the fluid will boil at the temperature of the hot surface and condense at the temperature of the cold surface—either at atmospheric pressure or in a partial vacuum.

A wick 36 on the inside of the heat pipe 30 facilities the return of the condensed fluid 100 to the hot end. The wick 36 is primarily needed when the fluid 100 must return by capillary action against gravity. The heat pipe 30 can sometimes be partially evacuated, a vent or other means known to those ordinarily skilled in the art, to adjust the boiling temperature of the working fluid 100.

In practice, heat pipes can achieve a thermal conductivity as high as one thousand times or more than that of a solid copper rod of the same dimensions. Heat pipes in production commonly have diameters of 3, 4, and 6 millimeters (metric), or ¼ and ⅝ inches (English). Flat heat pipes have been produced as thin as 0.5 millimeters.

Figure 4:
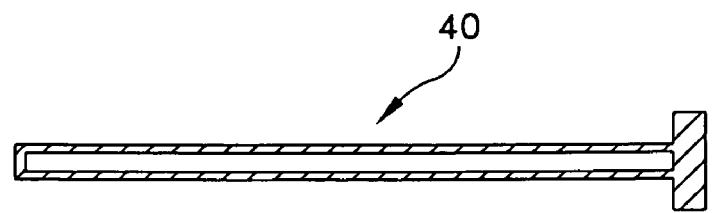
FIG. 4 depicts an embodiment of transducer cooling using the heat pipe of the present invention.

Heat pipes can be incorporated in several ways. For example, a center bolt 40 can be made hollow with an inner cavity (and incorporating a wick) so that it also acts as a heat pipe (See FIG. 4). This concept synergistically takes advantage of the requirement for reduced bolt stiffness (and hence, reduced bolt cross-sectional area).

The overall bolt diameter can increase to optimize heat transfer while appropriately reducing the wall thickness to give the bolt 40 for a proper mechanical stiffness. Hollowing the bolt will mainly reduce stiffness as defined as the change in force divided by the change in length. This often needed because the bolt should not be stiffer than the ceramic. In this sense, the invention achieves a degree of synergy. Converting the center bolt 40 to a heat pipe can substantially increase effective thermal conductivity. This increase in thermal conductivity has the effect of significantly increasing the heat flow from the stack interior to the thermally conductive end masses, which then conduct heat to the surrounding fluid.

Figure 5:
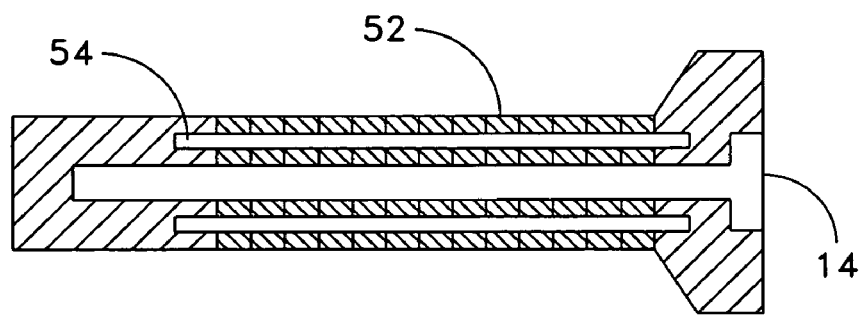
FIG. 5 depicts a first variant of the embodiment of the present invention.

As shown in FIG. 5, a variant of the present invention involves drilling additional holes into ceramic rings 52 and inserting heat pipes 54. The heat pipes 54 can be comparatively small in diameter compared to the diameter of the stack. The cross-sectional area is proportional to the square of the diameter. Again, this use of the heat pipes 54 has the effect of substantially increasing heat flow from the ceramic interior, where the heat is most needed. The reduction in ceramic volume (and thus the reduction in available power and mechanical stiffness) is minimal. This variant of the present invention has the advantage of avoiding redesign of the bolt 14.

Furthermore, increasing the length of the heat pipe 54 into the tail mass and the piston also increases the length of the "cool" region for the working fluid 100 to condense; thereby improving the performance of the heat pipe.

Figure 6:
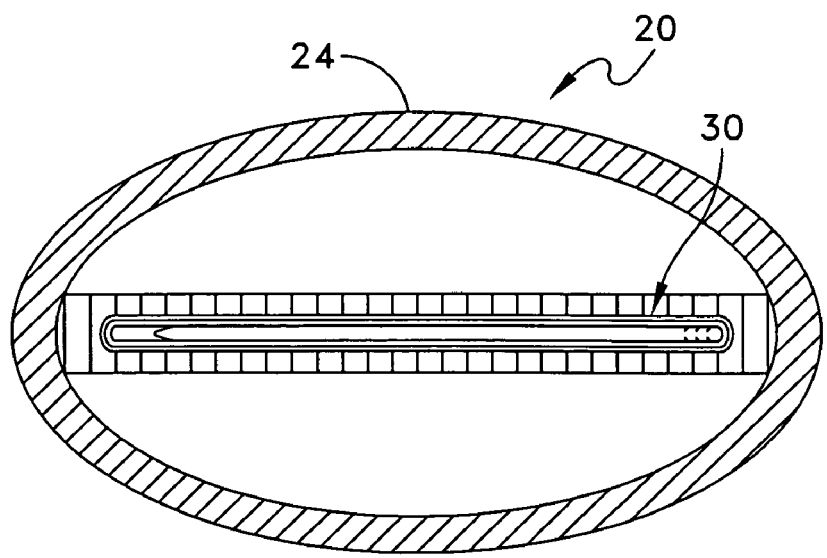
FIG. 6 depicts a further variant of the embodient of the present invention in which the variant involves flex tensional transducers.

A further variant of the present invention (involving flex tensional transducers; SEE FIG. 6) involves a heat pipe either in the center or in multiple locations in the ceramic rings to conduct heat to the shell. This use of heat pipes in the flex tensional transducer has the advantage that both ends of the heat pipe are thermally "shorted" to the surrounding fluid, but the disadvantage of a shorter "cool" region for the heat pipe.

The foregoing description of the preferred embodiments of the invention has been presented for purposes of illustration and description only. It is not intended to be exhaustive nor to limit the invention to the precise form disclosed; and obviously many modifications and variations are possible in light of the above teaching. Such modifications and variations that may be apparent to a person skilled in the art are intended to be included within the scope of this invention as defined by the accompanying claims.

What is claimed is:

1. An acoustic transducer, comprising:
   a tail mass at a first end of said transducer;
   a piston at a second end of said transducer;
   a plurality of ring elements between said tail mass and said piston to longitudinally connect said tail mass and said piston with each of said ring elements having a face matable to a face of another of said ring elements wherein said mated ring elements form a piezoceramic stack between said tail mass and said piston; and
   at least one closed heat pipe, said heat pipe longitudinally positioned within said stack and said piston with said heat pipe providing tension of said stack wherein said heat pipe contains a first quantity of fluid, said heat pipe having a first end and a second end with the first end contactable to a second quantity of fluid exterior to said transducer;
   wherein the first quantity of fluid proximate to the first end is capable of cooling from the second quantity of the fluid such that heat transmitted to a portion of the first quantity of fluid proximate to the second end of said heat pipe is cooled by a portion of the first quantity of fluid proximate to the first end.

2. The transducer in accordance with claim 1, wherein said heat pipe is integral to a center bolt that slidably fits into a center portion of said ring elements.

3. The transducer in accordance with claim 2, wherein said heat pipe portion of said center bolt has a thickness capable of optimizing stiffness of said center bolt such that a specified resonant frequency is maintained.

4. The transducer in accordance with claim 3, wherein at least two apertures are positioned within each of said ring elements with additional heat pipes positioned longitudinally thru said ring elements.

5. The transducer in accordance with claim 1, wherein the second end is in contact with said tail mass.

6. The transducer in accordance with claim 5, wherein the first end of said heat pipe is in contact with a portion of said transducer that is cooler than a portion of said transducer in contact with the second end of said heat pipe.

7. The transducer in accordance with claim 6, said heat pipe further comprising a wick positioned interior to the first quantity of fluid wherein said wick is capable of moving the first quantity of fluid by capillary action in the heat pipe.

8. The transducer in accordance with claim 1, wherein the first end of said heat pipe is in contact with a portion of said transducer that is cooler than a portion of said transducer in contact with the second end of said heat pipe.

9. The transducer in accordance with claim 8, said heat pipe further comprising a wick positioned interior to the first quantity of fluid wherein said wick is capable of moving the first quantity of fluid by capillary action in the heat pipe.

10. The transducer in accordance with claim 1, said heat pipe further comprising a wick positioned interior to the first quantity of fluid wherein said wick is capable of moving the first quantity of fluid by capillary action in the heat pipe.

11. A flextensional transducer with an elongated exterior shell, said flextensional transducer comprising:
    a plurality of ring elements with each of said ring elements having a face matable to a face of another of said ring elements wherein said mated ring elements form a ceramic stack between longitudinal ends of said elongated exterior shell; and
    at least one closed heat pipe, said heat pipe longitudinally positioned within said stack with said heat pipe providing tension of said stack wherein said heat pipe contains a first quantity of fluid contactable to a second quantity of fluid exterior to said transducer;
    wherein the first quantity of fluid is capable of cooling from the second quantity of the fluid;
    wherein said ceramic stack drives said shell by expansion and contraction thereby leading to larger displacement of the second quantity of fluid because of the shell geometry with the result of radiating acoustic energy.

\* \* \* \* \*